US006864231B2

(12) United States Patent
Chokshi

(10) Patent No.: US 6,864,231 B2
(45) Date of Patent: Mar. 8, 2005

(54) GLYCOPROTEIN MATRIX COMPOSITIONS AND METHODS RELATED THERETO

(75) Inventor: Dilip Chokshi, Parsippany, NJ (US)

(73) Assignee: Pharmachem Laboratories, Inc., Kearny, NJ (US)

(*) Notice: Subject to any disclaimer, the term of this patent is extended or adjusted under 35 U.S.C. 154(b) by 0 days.

(21) Appl. No.: 09/906,576

(22) Filed: Jul. 16, 2001

(65) Prior Publication Data

US 2002/0132761 A1 Sep. 19, 2002

Related U.S. Application Data

(63) Continuation-in-part of application No. 09/757,222, filed on Jan. 9, 2001.

(51) Int. Cl.[7] ................. A61K 38/16; A61K 35/00; A01N 65/00; C12P 1/00

(52) U.S. Cl. ............... 514/8; 424/115; 424/93.1; 424/93.3; 424/93.4; 424/93.45; 424/93.51; 424/780; 435/41; 435/42; 435/71.1; 435/71.2; 435/72; 435/73; 435/74

(58) Field of Search ............... 514/8; 429/429; 424/115, 93.1, 93.3, 93.4, 93.45, 93.51, 780; 435/123, 41, 42, 71.1, 71.2, 72, 73, 74, 75–79

(56) References Cited

U.S. PATENT DOCUMENTS

| | | | |
|---|---|---|---|
| 3,196,018 A | | 7/1965 | Galler |
| 4,654,373 A | | 3/1987 | Bertelli |
| 4,797,289 A | * | 1/1989 | Reddy ............... 426/43 |
| 5,008,118 A | | 4/1991 | Iwanami et al. |
| 5,441,737 A | | 8/1995 | Nitsche |
| 5,639,787 A | | 6/1997 | Riordan et al. |
| 5,747,071 A | | 5/1998 | Segall et al. |
| 5,773,011 A | | 6/1998 | Grubhofer |
| 5,827,886 A | | 10/1998 | Hersh |
| 5,891,469 A | | 4/1999 | Amselem |
| 5,912,272 A | | 6/1999 | Hoppe et al. |
| 5,950,634 A | | 9/1999 | Ochi et al. |
| 5,989,583 A | | 11/1999 | Amselem |
| 6,045,826 A | | 4/2000 | Borowy-Borowski et al. |
| 6,054,261 A | | 4/2000 | Masterson |
| 6,221,357 B1 | * | 4/2001 | Bok et al. ............ 424/195.1 |

FOREIGN PATENT DOCUMENTS

| | | |
|---|---|---|
| EP | 0409252 A2 | 1/1991 |
| EP | 0725077 A1 | 8/1996 |
| EP | 1064946 A2 | 1/2001 |
| WO | WO 96/17626 | 6/1996 |
| WO | WO 98/30583 | 7/1998 |
| WO | WO 00/43490 * | 7/2000 |

OTHER PUBLICATIONS

Dosti, R.; Jolly Roger's Orange Bread Melts in Mouth: [Home Edition] The Los Angeles Times (Pre–1997 Full-text), Feb. 1989 p. 34 (pp. 1–3 on ProQuest direct web site).*

Yahoo Slow Cooker Mail List; Cherry Yogurt Bread; newsgroup string published Jan. 8, 1999, www.groups.yahoo-.com/group/slowcooker/message/2396?source=1, pp. 1–3.*

Wikipedia Encyclopedia Online; Nutritional Information About the Apple; accessed on Oct. 20, 2003 from www.en.wikipedia.org/wiki/Apple/Nutritional information pp. 1–4.*

Faust, P. ;Hormones in the Gut– The Effect of Human Intestinal Bacteria on the Metabolism of Estrogen Hormones; accessed Oct. 20, 2003, copyrighted 2001, Paul Faust, N.D. Chesapeake Natural Health Center pp. 1–4.*

McGovern, S. Stonyfield Farm Yogurt Launches 'Big Gurt'; PR Newswire, New York, May 8, 1995 (pp. 1–2).*

Navarro, et al., "Protective Role in Ubiquinone in Vitamin E and Selenium–Deficient Plasma Membranes", *BioFactors 9*, pp. 163–170 (1999).

Hoppe, et al., "Coenzyme $Q_{10}$, a Cutaneous Antioxidant and Energizer", *BioFactors 9*, pp. 371–378 (1999).

Hodges, et al., "$CoQ_{10}$: Could It Have a Role in Cancer Management?", *BioFactors 9*, pp. 365–370 (1999).

Langsjoen, et al., "Overview of the Use of $CoQ_{10}$ in Cardiovascular Disease", *BioFactors 9*, pp. 273–284 (1999).

Baroni, et al., "Monounsaturated Diet Lowers LDL Oxidisability in Type Iib and Type IV Dyslipidemia Without Affecting Coenzymes $Q_{10}$ and Vitamin E Contents", *BioFactors 9*, pp. 325–330 (1999).

Pedersen, et al., "High Serum Coenzyme $Q_{10}$, Positively Correlated with Age, Selenium and Cholesterol, in Inuit of Greenland. A Pilot Study.", *BioFactors 9*, pp. 319–323 (1999).

Niibori, et al., "Bioenergetic Effect of Liposomal Coenzyme $Q_{10}$ on Myocardial Ischemia Reperfusion Injury", *BioFactors 9*, pp. 307–313 (1999).

(List continued on next page.)

*Primary Examiner*—Patricia Leith
(74) *Attorney, Agent, or Firm*—Hoffmann & Baron, LLP

(57) ABSTRACT

A composition is provided that includes a biologically active compound bound by a glycoprotein matrix. A method is also provided for the manufacture of a composition of the invention. The glycoprotein matrix can be formed by permitting the growth of glycoprotein producing bacteria in the presence of the active ingredient. The composition of the invention provides a method for increasing the stability and bioactivity of the active ingredient. A method is also provided for administering an active ingredient to a host by utilizing a composition of the invention.

10 Claims, No Drawings

OTHER PUBLICATIONS

Tomasetti, et al., "Distribution of Antioxidants Among Blood Components and Lipoproteins: Significance of Lipids/CoQ$_{10}$ Ratio as a Possible Marker of Increased Risk for Atherosclerosis", *BioFactors 9*, pp. 231–240 (1999).

Chida, et al., "In vitro Testing of Antioxidants and Biochemical End–Points in Bovine Retinal Tissue", *Ophthalmic Research*, 31: 407–415 (1999).

Bianchi, et al., "Oxidative Stress and Anti–Oxidant Metabolites in Patients with Hyperthyroidism: Effect of Treatment", *Horm. Metab. Res.*, 31: 620–624 (1999).

Al–Bekairi, et al., "Coenzyme Q$_{10}$ Ameliorates the Hepatic Toxicity Induced by Carbon Tetrachloride in Mice", *Research Communications in Pharmacology and Toxicology*, vol. 4, Nos. 3 & 4, pp. 163–171 (1999).

Yokoyama, et al., "Coenzyme Q$_{10}$ Protects Coronary Endothelial Function from Ischemia Reperfusion Injury Via an Antioxidant Effect", *Surgery*, vol. 120, No. 2, pp. 189–196 (1996).

Morita, et al., "Studies of Hypoxemic/Reoxygenation Injury: Without Aortic Clamping VII. Counteraction of Oxidant Damage by Exogenous Antioxidants: Coenzyme Q$_{10}$", *The Journal of Thoracic and Cardiovascular Surgery*, vol. 110, No. 4, Part 2, pp. 1221–1227 (1995).

Lass, et al., "Effects of Coenzyme Q$_{10}$ and α–Tocopherol Administration on Thier Tissue Levels in the Mouse: Elevation of Mitochondrial α–Tocopherol by Coenzyme Q$_{10}$", *Free Radical Biology & Medicine*, vol. 26, Nos. 11/12, pp. 1375–1382 (1999).

Nielsen, et al., "No Effect of Antioxidant Supplementation in Triathletes on Maximal Oxygen Uptake, $_{31}$P–NMRS Detected Muscle Energy Metabolism and Muscle Fatigue", *Int. J. Sports Med.*, 20: 154–158 (1999).

Alleva, et al., "Oxidation of LDL and Their Subfractions: Kinetic Aspects and CoQ$_{10}$ Content", *Molec. Aspects Med.*, vol. 18 (Supplement), pp. S105–s112 (1997).

Tomasetti, et al., "Coenzyme Q$_{10}$ Enrichment Decreases Oxidative DNA Damage in Human Lymphocytes", *Free Radical Biology & Medicine*, vol. 27, Nos. 9/10, pp. 1027–1032 (1999).

Aejmelaeus, et al., "Ubiquinol–10 and Total Peroxyl Radical Trapping Capacity of LDL Lipoproteins During Aging: the Effects of Q–10 Supplementation", *Molec. Aspects Med.*, vol. 18 (Supplement), pp. s113–s120 (1997).

* cited by examiner

GLYCOPROTEIN MATRIX COMPOSITIONS AND METHODS RELATED THERETO

This application is a continuation-in-part of application Ser. No. 09/757,222 filed on Jan. 9, 2001.

BACKGROUND OF THE INVENTION

Glycosylated proteins are present in the extracellular matrices and cellular surfaces of many cells. Glycoproteins are organic compounds composed of both a protein and a carbohydrate joined together by a covalent linkage. The oligosaccharide moieties of the glycoprotein are implicated in a wide range of cell-cell and cell-matrix recognition events.

The addition of the carbohydrates on the protein involves a complex series of reactions that are catalyzed by membrane-bound glycotransferases and glycosidases. The types and amounts of sugars that are attached to a given protein depend on the cell type in which the glycoprotein is expressed. In addition, the types of linkage used to join various sugar groups together also confound the complexity of glycosylation.

The biological activities of many glycoproteins are not detectably different if the carbohydrates are removed. However, glycosylation of proteins may have several effects. Carbohydrates often lengthen the biological life of a protein by decreasing the protein's rate of clearance from the blood. In addition, the carbohydrates may help the protein to fold properly, stabilize the protein, or affect physical properties such as solubility or viscosity.

It is estimated that 40% of the United States population are consuming nutritional supplements (for example, vitamins and minerals) (Meyers D G, et al. 1996. *Arch Intern Med.* 156:925). These supplements are ingested to compensate for inadequacies in ones diet and for the health benefits they provide. In addition, in certain situations in the medical, home health care, and nursing home facilities, patients are given either an enteral or parenteral feeding mixture which contain vitamins and minerals.

The absorption of various vitamins and minerals are affected by numerous factors, including diet. For example, high intakes of iron, zinc, or manganese can interfere with cooper absorption (Johnson M A, et al. 1998: *Am. J. Clin. Nutr.* 67:1035S). Furthermore, the absorption of iron from the diet is extremely poor. Several dietary factors can enhance the absorption of iron, including vitamin C (Zijp I M, et al., 2000. *Crit. Rev. Food Sci. Nutr.* 40:371) and vitamin A (Layrisse M, et al. 2000. *Arch Latinoam. Nutr.* 50:243).

However, the stability of various vitamins (including vitamin C and vitamin A) and mineral are degraded by several environmental factors. For example, vitamin C is degraded by oxygen present in the atmosphere (Nagy S. et al. 1977. *J. Argic. Food Chem.* 25:135). Moreover, vitamin A is degraded by photolysis while vitamin E is degraded by photo-oxidation (Allwood M C et al. 2000. *Clin. Nutr.* 19:339).

Analysis of parenteral nutrition mixtures during infusion in daytime administration demonstrated that vitamin A loss occurs rapidly during infusion, resulting in up to 80% loss in 6 hours. This loss in vitamin A was also observed with protection of the vitamin from light (Allwood M C et al. 2000. *Clin. Nutr.* 19:339).

Another study examined vitamin A levels of enteral feeding formulas stored in the dark. These feeding bags provide a vitamin A level that is 1.6 times above that of the U.S. daily recommendation. After 9 months of storage, the vitamin A level dramatically dropped to 0.2 to 0-fold of the U.S. daily recommendation (Frias J. et al. 2001. *J. Agric. Food Chem.* 49:2313).

Therefore, there is a need for compositions containing biologically active ingredients with an improved bioactivity and stability and methods of making such compositions.

SUMMARY OF THE INVENTION

In accordance with the present invention, glycoprotein matrix compositions are provided. The compositions include a glycoprotein matrix bound to a biologically active ingredient. In a preferred embodiment, the biologically active ingredients include CoEnzyme Q10 ($CoQ_{10}$), L-Carnitine base, minerals, and vitamins, such as Cyanocobalamin B12.

The glycoprotein matrix can be produced by microorganisms, such as yeast or bacteria. Preferred microorganisms are *Saccharomyces cervisiae* and bacteria within the genus *Lactobacillus*. The composition of the invention can also include stabilizers or additives to improve its properties. For example, in a preferred embodiment, the composition of the invention also includes a bioflavanoid, such as hesperidin, as a stabilizer.

A nutritional supplement is also provided. Such supplements are often referred to as "nutriceuticals." As indicated above, the biologically active ingredient can include those that have been shown to be beneficial for health. The nutritional supplement includes the glycoprotein matrix composition of the invention, having a glycoprotein matrix bound to the active ingredient.

A method is also provided for preparing a glycoprotein matrix containing composition. The method includes binding the a glycoprotein matrix to at least one biologically active ingredient. In a preferred embodiment, the glycoprotein matrix is formed by glycoprotein producing microorganisms. Thus, the binding includes contacting the active ingredient with a glycoprotein producing microorganism under conditions such that the microorganism will produce glycoprotein.

The glycoprotein containing composition of the invention demonstrates improved properties as compared to commercially available active ingredients not bound to glycoprotein matrix. Thus, a method is also provided for increasing the bioactivity of an active ingredient. A separate method is similarly provided for increasing the stability of an active ingredient. Both methods include binding the active ingredient to a glycoprotein matrix.

A method is also provided for delivering a biologically active ingredient to a host. The method includes binding the active ingredient with a glycoprotein matrix to form a glycoprotein matrix containing composition and administering the composition to the host.

DETAILED DESCRIPTION OF THE INVENTION

In accordance with the present invention, a composition is provided which includes a glycoprotein matrix and a biologically active ingredient. The composition of the invention provides improved stability and bioactivity characteristics of the active ingredient.

In a composition of the invention, a glycoprotein matrix is bound to at least one biologically active ingredient. The glycoprotein matrix and active ingredient can be associated with each other physically and/or chemically, such as by chemical reaction, and/or secondary chemical bonding, e.g., Van der Waals forces, etc. It is believed that glycoprotein matrix is bound to the active ingredient by weak covalent bonds.

For purposes of the present invention, the term "biologically active" means any material that affects the life processes of an organism, preferably a mammal. For example, the biologically active ingredient can include a drug or pharmaceutical, vitamin, mineral, chemical compound, etc. Examples of suitable chemical compounds include $CoQ_{10}$, and L-Carnitine base. Examples of suitable minerals include selenium, chromium, zinc, iron and other standard minerals consumed by humans as a nutritional supplement. Examples of suitable vitamins include Vitamins C, E, A, and other vitamins consumed by humans as a nutritional supplement.

The composition can contain essentially any percentage of biologically active ingredient as desired. For example, the percentage of active ingredient can vary between 0.1 and 99% by weight of the composition depending upon the active ingredient and the desired result in the host.

The glycoprotein matrix is the glycoprotein to which the active ingredient is bound. Glycoprotein is a composite material made of a carbohydrate group and a simple protein. Glycoprotein matrix is a molecular network comprised of a plurality of glycoprotein molecules bound together.

The carbohydrate in the glycoprotein can be any suitable carbohydrate, such as a monosaccharide, disaccharide, oligosaccharide, or polysaccharide. Oligosaccharide is preferred. The protein of the glycoprotein can any suitable polypeptide. The ratio of carbohydrate to protein in the glycoprotein matrix can vary, for example, from 99:1 to 1:99 by weight. A ratio of approximately 1:1 is preferred.

The ratio of glycoprotein matrix to active ingredient can also vary. It is preferred that the ratio of glycoprotein matrix to active ingredient will be such that all or nearly all of the active ingredient in the composition is bound by glycoprotein matrix. To ensure that essentially all of the active ingredient is bound, higher ratios of glycoprotein matrix to active ingredient can be used. The invention also contemplates a composition where there may be insufficient glycoprotein to bind all of the active ingredient. In such cases, the ratio of glycoprotein matrix to active ingredient can be less.

In a preferred embodiment, the source of the glycoprotein matrix is a microorganism and, therefore, a preferred composition of the invention will include microorganisms. At the end of the manufacturing process of the composition, these microorganisms are usually inactive.

As discussed more specifically below, the glycoprotein matrix can be bound to the active ingredient by allowing the microorganism to ferment, in the presence of the active ingredient. As used herein, fermentation is the process by which microorganisms metabolize raw materials, such as amino acids and carbohydrate, to produce glycoprotein.

The microorganisms produce glycoprotein both intracellularly and extracellularly The intracellular glycoprotein will mainly be located in the cytoplasm of the microorganism or become part of the microorganism's physical structure. The glycoprotein from the microorganism that forms the glycoprotein matrix is mainly extracellular and, therefore, is available to be bound to the active ingredient. Intracellular glycoprotein can also be made accessible for binding to active ingredient by rupture of the microorganisms after glycoprotein production.

Microorganisms that produce a glycoprotein matrix include, but are not limited to, yeast and some bacteria. A preferred yeast is *Saccharomyces cervisiae*. Bacteria that produce glycoprotein include bacteria within the genus *Lactobacillus*. For example, such bacteria include, but are not limited to, *Lactobacillus acidophillus, Lactobacillus bulgaricus, Lactobacillus caucasicus*, and *Bacterium bifidus*. Preferred bacteria include *Lactobacillus acidophillus*, and *Bacterium bifidus*.

The composition of the invention can also include pharmaceutically acceptable buffers, excipients, diluents, surfactants, adjuvants, flavorings, and the like. One example of an adjuvant is a bioflavanoid. A bioflavanoid is a group of naturally occurring substances thought to maintain normal conditions in the walls of small blood vessels. Bioflavanoids are widely distributed among plants, especially citrus fruits (hesperidin), black currants (rutin) and rose hips (quercitin). The bioflavanoid can also act to increase the production of glycoprotein by the microorganism and increase stability of the active ingredient. A preferred bioflavanoid is hesperidin. The amount of bioflavanoid should be sufficient to achieve the desired stabilizing results.

Other additives can include, for example, natural sources of the bioactive ingredient, such as a vitamin or mineral. Example of natural sources of an active ingredient include carrot powder for beta carotene and alfalfa herb for Vitamin K and folic acid.

The invention also includes a nutritional supplement that includes a composition of the invention as described above. As indicated above, many of the possible active ingredients include substances, such as vitamins and minerals, consumed to supplement nutrition. Thus, the nutritional supplement should contain an amount of the composition such that a sufficient amount of active ingredient is administered to achieve the desired result. Such amounts can be determined by one skilled in the art.

The composition of the invention can be manufactured so as to be biocompatible. Since the nutritional supplement is to be ingested, the microorganism used to produce the glycoprotein matrix should be suitable for consumption by mammals, especially humans. Examples of such microorganisms include *Lactobacillus acidophillus* and *Saccharomyces cervisiae*. The nutritional supplement can also include pharmaceutically acceptable buffers, excipients, diluents, adjuvants, flavorings, and the like.

A method of preparing a glycoprotein matrix containing composition is also provided. The method includes binding a glycoprotein matrix to at least one biologically active ingredient.

In a preferred embodiment, the binding of the glycoprotein matrix to the ubiquinone includes contacting the ubiquinone with a glycoprotein producing microorganism under conditions in which the microorganism produces glycoprotein. The microorganisms require a medium in which to ferment and produce glycoprotein. Such media are known to those skilled in the art, and are usually liquid. Water is preferred. The microorganism solution should contain enough growth medium so as to allow for efficient growth of the microorganisms, as is known in the art. When the microorganisms are added to the liquid medium, a microorganism solution is formed.

A microorganism solution is prepared in which the microorganisms will produce glycoprotein. The microorganisms are added to an appropriate medium that will allow microorganism growth, such as $H_2O$. The number of colony forming units of microorganism added to the medium will vary based upon the type of microorganism used. Any suitable microorganism can be used that produces a glycoprotein matrix. It is preferred that the microorganism used be acceptable for administration to humans and mammals and, more preferably, be acceptable for consumption. For example, *Saccharomyces cervisiae*, also known as baker's yeast, can be used as the first microorganism.

Combinations of microorganisms can be used provided that at least one of the microorganisms produces glycoprotein. When using combinations of microorganisms, the growth of one type of microorganism should not prevent the growth of the other. For example, various types of different yeast that produce glycoprotein can be used. Also, yeast and bacteria can be combined to produce glycoprotein. This combination is particularly advantageous because various types of bacteria, such as *Lactobacillus acidophillus*, also produce glycoprotein.

A sufficient amount of colony forming units should be added to the microorganism solution to bind at least some of the active ingredient. If the composition of the invention is to contain a small amount of active ingredient, fewer microorganisms will be required to bind the active ingredient with glycoprotein matrix. It is preferred that enough colony forming units be added to the microorganism solution to bind essentially all of the active ingredient with glycoprotein matrix. One skilled in the art can determine such amounts.

The amount of colony forming units of the microorganism utilized can also depend upon the molecular weight and amount of the active ingredient in the composition. For example, more colony forming units are necessary to fully bind a higher molecular weight molecule that makes up a relatively high weight percentage of the final composition, such as $CoQ_{10}$. Fewer colony forming units are required for a composition that includes a low molecular weight molecule or trace amount of an element as the active ingredient, such as selenium.

The microorganisms that produce the glycoprotein typically require nutrients to efficiently grow, multiply, and form glycoprotein by metabolizing the nutrients. The nutrients can be directly added to the microorganism solution or can be added to a nutrient media, which is then added to the microorganism solution.

Amino acids are one nutrient that may be necessary for efficient glycoprotein production. The amino acids are metabolized by the microorganisms and ultimately become part of the polypeptide within the glycoprotein matrix. The amino acids should include those that are suitable for the manufacture of glycoprotein. Such amino acids include, but are not limited to, glutamine, lysine, cysteine and methionine, aspartic acid, leucine, valine, alanine, arginine, and glycine. The amino acids need not be in a pure form, but can be added as part of a stable compound. Examples of amino acid compounds that can be used are L-Glutamic Acid, L-Lysine HCl, L-Cysteine HCl and DL-Methionine.

The amount of amino acids will vary based upon the amount, molecular weight, and percentage of active ingredient desired to be bound by glycoprotein matrix. If the active ingredient is a small molecular weight molecule or if only a trace is to be utilized as the active ingredient, it may not be necessary to add amino acids as a nutrient for the production of glycoprotein matrix by the microorganisms. For example, if trace elements, such as selenium, chromium, vanadium, moybdenum, nickel, etc. are used as the active ingredient, the microorganisms can often produce enough glycoprotein matrix to bind the active ingredient by metabolizing the carbohydrate without the need to feed the microorganisms amino acids. If a macromolecule, such as $CoQ_{10}$ is utilized as the active ingredient, the addition of amino acids is preferred in order to enhance glycoprotein matrix production.

Carbohydrate is a nutrient that is added for the efficient production of glycoprotein by the microorganism. As with the amino acids, the carbohydrate can be added to a nutrient media, which is then added to the microorganism solution, or can be added directly to the microorganism solution. Carbohydrates beneficial for the production of glycoprotein are known in the art. The carbohydrate can be, for example, a polysaccharide, oligosaccharide, disaccharide or monosaccharide or combinations thereof. Examples of appropriate carbohydrates include, but are not limited to, maltose and gum acacia. Maltose is most preferred.

The amount of carbohydrate added to the nutrient media or microorganism solution will vary depending upon the complexity and molecular weight of the carbohydrate added to the solution. The amount of carbohydrate should be sufficient to permit the microorganisms to produce the glycoprotein matrix. The amount of carbohydrate necessary will also vary based upon the amount and percentage of active ingredient desired to be bound by glycoprotein matrix.

The binding of the active ingredient occurs in the microorganism solution as the glycoprotein is being produced by the microorganisms. Thus, the microorganism solution will contain the active ingredient to be bound by glycoprotein matrix. The active ingredient is added before or soon after fermentation of the microorganisms begins.

The method of the invention can include the addition of pharmaceutically acceptable buffers, excipients, diluents, surfactants, adjuvants, flavorings, and the like. These additives can be added at any time during the method of manufacture of the composition. For example, it may be desirable to utilize a surfactant to ensure even distribution of the active ingredient.

If desired, appropriate additives may be included to the microorganism solution. The amount of additive would be the amount necessary to obtain the desired beneficial result, without diminishing the viability of the microorganism or the production of glycoprotein by the microorganism. The amounts of such additives can be determined by one skilled in the art.

Such additives may include, for example, stabilizers. Stabilizers are substances that improve the stability of the active ingredient. One example of such a stabilizer is bioflavanoids. Preferred bioflavanoids include hesperidin, quercitin and rutin. Since these bioflavanoids are naturally obtained, commercially available bioflavanoids very often will include additional materials such as fibers or cellulose. The active portion, e.g. hesperidin, quercitin, or rutin, will make up a percentage of the bioflavanoid.

Additives can also include, for example, natural sources of the active ingredient to be administered. Other additives can be added which, for example, improve the viability of the microorganisms that produce the glycoprotein or increase the yield of glycoprotein that becomes bound to the active ingredient. For example, salts can be added in order to increase the viability of the microorganism. Such salts include, but are not limited to, calcium carbonate, ammonium sulfate, and magnesium sulfate. Calcium carbonate is preferred. The amount of salt added to the microorganism solution should be sufficient to obtain the desired result of improving the viability of the organism, as is known in the art. A preferred range of salt added to the microorganism solution is between about 25 to about 150 grams of salt per 375 grams of microorganism, such as *Saccharomyces cerivisiae*. Approximately 40 g of salt per 375 gram of microorganism is most preferred.

In a preferred embodiment, substances are added to the microorganism mixture that will further induce the growth of the microorganisms and the fermentation resulting in the formation of a glycoprotein matrix. For example, it may be beneficial to add a nutritional substance to the microorganism mixture. Examples of such nutritional substances include soy flour and nutritional yeast, such as inactive baker's yeast or inactive brewer's yeast. When using soy four, non-genetically modified organism (non-GMO) soy flour is preferred. Such nutritional substances feed the microorganisms, thereby inducing growth and the manufacture of glycoprotein.

The method of the invention does not require that the ingredients ultimately forming the microorganism solution be added in any particular order. For example, as discussed above, the amino acids and carbohydrate metabolized by the microorganisms can each be added to a nutrient media that is added to the microorganism solution or can be added directly to the microorganism solution. Also, the active ingredient can be directly added to the microorganism solution or can be added to a nutrient media that is then added to the microorganism solution.

If a nutrient media is prepared, it an include amino acids as well as other ingredients; for example, the active ingredient, carbohydrate, salt, and stabilizer. Also, in order to create a more homogenous nutrient media, the temperature of the nutrient media can be raised. However, the temperature of the nutrient media should remain below the temperature at which the components of the nutrient media will decompose. For example, a nutrient media containing amino acids, $CoQ_{10}$ and bioflavanoid can be heated to a temperature of about 130° F. before being added to the microorganism solution. If the nutrient media is heated, it should be allowed to cool, e.g. to about 95° F., before being added to the microorganism solution. Also, the nutrient media should be added slowly to the microorganism solution so as to minimize the disturbance of the microorganisms in solution.

The microorganism solution should be maintained under conditions that permit optimal microorganism growth. For example, a temperature range of between about 90–95° F. is suitable for most glycoprotein producing microorganisms. The microorganisms should also be permitted to ferment for a sufficient period of time to produce the desired amount of glycoprotein matrix. As discussed above, this time will vary based upon, among other factors, the amount and percentage of active ingredient to be bound by glycoprotein matrix. For example, in order to fully bind 475 g $CoQ_{10}$, applicants allowed a microorganism solution containing 375 g active baker's yeast to ferment for approximately four hours at 90–95° F.

In a preferred embodiment, a proteolytic enzyme is added to the microorganism solution after the microorganisms in the microorganism solution have been permitted to ferment. Suitable proteolytic enzymes include, but are not limited to, papain, bromelain, pepsin or fungal protease. Without being bound by theory, it is believed that the proteolytic enzymes assist in breaking down the cell wall of the microorganisms. This breaking down of the cell wall of the microorganism may help in releasing the glycoprotein produced by the microorganism and improves the digestibility of the final composition in humans.

The amount of proteolytic enzyme added to the microorganism solution should be sufficient to break down the cell wall of the first microorganism, but should not affect the integrity of the glycoprotein produced by the microorganism. This amount will vary depending upon the number of microorganisms in the microorganism solution. Typically, approximately 1 to 50 g of proteolytic enzyme will be added per 500 g microorganism.

Additional microorganisms can be added to the microorganism solution after the first microorganisms are added. It is preferred that the additional microorganisms be added after the first microorganisms have been permitted to ferment, but before the microorganism solution has been dehydrated. In a preferred embodiment, the additional microorganisms also produce glycoprotein. Additional microorganisms can also include microorganisms that improve digestibility of the components of the composition, such as the glycoprotein, or enhance the bioavailability of the active ingredient.

After the additional microorganisms are added to the microorganism solution, the solution should be maintained at a temperature and conditions so as to permit the growth and fermentation of both the first and additional microorganisms. Such conditions are known in the art and will usually coincide with the growth conditions for the first microorganisms, as discussed above.

Bacteria can be utilized as an additional microorganism. As with the first microorganisms, it its preferred that the additional microorganisms be suitable for administration to mammals and, more preferably, suitable for human consumption. Examples of such bacteria are bacteria of the genus *Lactobacillus*, for example *Lactobacillus acidophillus*. Amounts of the additional organism, such as *Lactobacilli*, can vary. It is usually preferred that at least 4 billion colony forming units per gram of microorganism used for each 100 grams of total composition.

*Lactobacilli* are present at birth as part of the intestinal microflora. This microflora is constantly changing depending on lifestyle, diet and influence from the environment. *Lactobacilli* are involved in various metabolic functions, and can improve digestibility of food components and enhance bioavailability of nutrients. They can also control fermentative production of amine indole.

Due to the medium used to grow the microorganisms, the microorganism solution will usually be in the form of an aqueous mixture or solution. When the microorganism solution is in the form of an aqueous solution, it is preferred that the microorganism solution be dehydrated after fermentation has taken place and the active ingredient has been bound by the glycoprotein matrix. Methods of dehydrating solutions are known in the art. For example, such methods include freeze-drying, spray drying, open air drying, and drum drying. Spray drying is preferred. A longer dry time may be necessary depending on various factors, such as total water content, equipment used, and atmospheric humidity. However, after dehydrating the microorganism solution, the resulting product should be a fine powder, which can then be manufactured into a pill or other form suitable for administration.

The microorganism solution can be homogenized to produce a more uniform product. The homogenization is performed after the production of glycoprotein matrix, usually before dehydrating the microorganism solution. Methods of such homogenization are known in the art. For example, homogenization can be performed by a homogenization pump, shearing pump or, if produced in a small batch, a blender.

In a preferred embodiment, the microorganisms are deactivated before dehydrating, preferably by raising the temperature of the microorganism solution. For example, the preferred temperature and conditions for stopping the fermentation in a mixture containing *Saccharomyces cervisiae* and *Lactobacillus* bacteria is heating the mixture to approximately 160 to 170° F. for approximately three hours with stirring.

It has been discovered that binding an active ingredient to a glycoprotein matrix as in the composition described can increase the bioactivity of the active ingredient. Therefore, a separate embodiment of the invention includes a method for increasing the bioactivity of an active ingredient by binding the active ingredient with a glycoprotein matrix. The glycoprotein matrix composition of the invention will allow the active ingredient to have an increased effect on the organism to which the composition is administered.

For example, it is known that $CoQ_{10}$ can have an antioxidative effect. As described in Example 2, compositions of the invention having $CoQ_{10}$ bound to a glycoprotein matrix were found to have antioxidant activity approximately 20 times that of commercial $CoQ_{10}$. The composition of the invention having selenium as the active ingredient demonstrated antioxidant activity 64 times better than commercially available selenium, as further described in Example 5.

It has also been discovered that binding the active ingredient to a glycoprotein matrix as in the composition of the invention can increase the stability of the active ingredient. Therefore, a separate embodiment of the invention includes a method for increasing the stability of an active ingredient by binding the active ingredient with a composition of the invention.

For example, $CoQ_{10}$ can deteriorate when exposed to air. By binding the $CoQ_{10}$ with a glycoprotein matrix, this deterioration is decreased. As demonstrated in Example 3, the composition of the invention lost only half as much $CoQ_{10}$ over 36 days compared to commercial $CoQ_{10}$ when exposed to open air at 50° C.

In a separate embodiment, a method of delivering an active ingredient to a host is provided. The method includes binding a glycoprotein matrix to the active ingredient to form a glycoprotein matrix composition. The composition is then administered to the host.

The glycoprotein matrix composition containing an active ingredient can be administered topically or systemically. Systemic administration can be enteral or parenteral. Enteral administration is preferred. For example, the composition can be easily be administered orally. Liquid or solid (e.g., tablets, gelatin capsules) formulations can be employed. The formulation can include pharmaceutically acceptable excipients, adjuvants, diluents, or carriers. The composition can also be administered intravenously, with a suitable pharmaceutical carrier (vehicle) or excipient, as understood by those skilled in the art. Topical administration can be, for example, in a cream or emollient. Sustained release formulations, as are known in the art, can also be incorporated into the composition.

In a preferred embodiment the host is a mammal. Mammals include, for example, humans, as well as pet animals such as dogs and cats, laboratory animals such as rats and mice, and farm animals such as horses and cows. Humans are most preferred.

EXAMPLE 1

This example demonstrates the preparation of a composition of the invention utilizing $CoQ_{10}$ as the active ingredient. The particular method employs 5 kilograms of dry material to yield approximately 4 kg of the composition.

A nutrient media containing $CoQ_{10}$ was first prepared. 110 g L-Glutamic Acid, 212 g L-Lysine HCl, 535 g DL-Methionine, and 45 g L-Cysteine HCl, and 40 g calcium carbonate were added slowly to 4 liters $H_2O$ heated to 140° F. After 30 minutes, 475 g CoQ was added to the amino acid solution. The solution was stirred at about 130° F. for approximately 4 hours and allowed to cool to 95+/−2° F. 825 g of a natural bioflavanoid having 300 g hesperidine was then added.

An active yeast solution was then prepared. 375 g active baker's yeast, *Saccharomyces cervisiae* (~10 billion colony forming units per gram) was added to 4 liters $H_2O$ to form an aqueous solution. 125 g maltose and 625 g gum acacia were then added.

The nutrient media containing $CoQ_{10}$ was then inoculated very slowly into the active yeast solution to form a live fermented solution. The mixture was allowed to ferment for four hours at 90–95° F. 500 g nutritional yeast (inactive Baker's Yeast) and 1003 g soy flour (non-GMO) were added and the mixture was allowed to ferment for four hours at 90–95° F. 5 g proteolytic enzyme (Papain) was then added and allowed to react for 30 minutes.

125 g *Lactobacillus acidophillus* and *Bacterium bifidus* (~4 billion colony forming units/gram) were added to the live fermented solution and allowed to ferment for 1½ hours at 95+/−2° F. with constant stirring. Active fermentation was then stopped by heating the solution to 160–170° F. for three hours with stirring.

The solution was then homogenized in a shearing pump (Charles Ross & Sons Corp.) for approximately 1–2 hours and spray dried (NIRO, Nicholas Engineers Research Corp.) for approximately 4 hours. The resulting product was a fine brown to tan powder, which was analyzed for stability and bioactivity.

EXAMPLE 2

The bioactivity of a composition of the invention produced in Example 1 was examined relative to commercially available $CoQ_{10}$ (USP).

A weighed portion (50–500 mg) of solid sample of the composition of the invention was mixed with 5 ml of 50% methanol/water and heated at 90° C. in a plastic screw-capped tube with intermittent shaking for 2 hours to determine the unconjugated ("free") phenols present. Another weighed portion of the same sample was heated with 5 ml of 1.2 M HCl in 50% aqueous methanol for 2 hours at 90° C. to measure the unconjugated plus conjugated ("total") phenols. The extracts, each done in duplicate, were then filtered with a 0.45 µm filter and stored at −20° C. until assay.

Values for free polyphenols and total phenols for commercial $CoQ_{10}$ are known.

The phenol content in the extracts was measured by the Folin-Cocialteu reagent (Sigma Chemical Co., St. Louis, Mo.) using catechin (Sigma) as a standard. A blank, catechin standards and samples were added to the Folin reagent in a cuvette and after 20 minutes the color was measured at 720 nm vs. a blank.

Quality of antioxidant activity was determined in a dose-response assay of the $IC_{50}$ value, i.e. the concentration of phenols in the extract to inhibit 50% of the oxidation of lower density lipoproteins (LDL+VLDL). This model is an in vitro model of artherosclerosis where the initial step is the oxidation of the lower density lipoproteins, i.e. the "bad" cholesterol. LDL+VLDL is isolated from the plasma of normocholesterolemic humans using an heparin-agarose affinity column (H-6508, Sigma). Extracts of antioxidants were added in duplicate at various concentrations (typically 0.05 to 15 $\mu$M) to LDL+VLDL (70 $\mu$g/ml of protein as measured vs. albumin standard with Coomasie Blue, Sigma). 25 $\mu$M of the oxidant cupric ion was then added, the solution made to a total volume of 400 $\mu$L with phosphate buffered saline, pH 7.4 (Sigma) and the solution left at 37° C. for 6 hours.

The amount of lipid peroxides was measured using thiobarbituric acid and fluorometry. The % of inhibition of lipid peroxide formation was calculated vs. a control with no added antioxidants. The $IC_{50}$ value in $\mu$M units was then calculated.

The amount of $CoQ_{10}$ in the composition of the invention was determined by HPLC using UV detector, C18 column (Perkin Elmer Pecosil 5, 15 cm) and a solvent of 75% methanol and 25% isopropanol.

The results are set forth in Table 1 below. The higher the $1/IC_{50}$ value, the better the quality of antioxidants.

The methods used are further described in: Vinson, J. A., and Hontz, B. A. Phenol antioxidant index: comparative antioxidant effectiveness of red and white wines, *J. Agric. Food Chem.*, 1995, 43, 401–403; Vinson, J. A., Jang, J., Dabbagh, Y. A., Serry, M. M., and Cai, S. Plant polyphenols exhibit lipoprotein-bound antioxidant activity using an in vitro model for heart disease. *J. Agric. Food Chem.*, 1995, 43, 2798–2799; and Steinberg, D., Parthasarathy, S., Carew, T. E., Khoo, J. C., and Witzum, J. L. Beyond cholesterol: modification of low density lipoprotein that increases its atherogenicity. *New Eng. J. Med.*, 1989, 320, 915–924; all of which are incorporated herein by reference.

TABLE 1

| SAMPLE | IC50 (uM) | 1/IC50 |
|---|---|---|
| $CoQ_{10}$ bound by glycoprotein contains 8.4% $CoQ_{10}$ | 0.064 (based on $CoQ_{10}$ conc.) | 15.6 |
| $CoQ_{10}$ (USP) | 1.33 | 0.751 |

The results demonstrate that the $CoQ_{10}$ composition of the invention bound to glycoprotein has an antioxidant activity that is 20 times better than commercially available $CoQ_{10}$.

EXAMPLE 3

The stability of the composition obtained in Example 1 was examined.

100 mg of USP $CoQ_{10}$ (Sigma) and a composition from Example 1 was placed in a 10 ml beaker in a 50° C. oven open to the air. The amount of $CoQ_{10}$ remaining was analyzed by HPLC using a C18 column (Perkin Elmer Pecosil 5, 15 cm) and a solvent of 75% methanol and 25% isopropanol. The results are set forth below in Table 2.

TABLE 2

| Sample | Loss of $CoQ_{10}$ at 0 days | Loss of $CoQ_{10}$ after 36 days at 50° C. (equivalent to 3 months at room temperature) | Loss of $CoQ_{10}$ after 72 days at 50° C. (equivalent to 6 months at room temperature) |
|---|---|---|---|
| USP $CoQ_{10}$ | 0% | 6.8% | 16.8% |
| $CoQ_{10}$ bound by glycoprotein | 0% | 3% | 14.7% |

After 36 days, the composition of the invention lost only half as much as the commercial $CoQ_{10}$ material, i.e. 3% vs. 6.8%. After 72 days, the composition of the invention lost 14.7% of its $CoQ_{10}$ vs. 16.8% $CoQ_{10}$ lost with the commercial sample.

Therefore, the results show that the composition of the invention serves to increase the stability of the $CoQ_{10}$ contained therein.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

EXAMPLE 4

This example demonstrates the preparation of a composition of the invention utilizing selenium as the active ingredient. The particular method yielded 100 kilograms of selenium containing composition.

A nutrient solution containing Selenium was first prepared. 312 grams Selenium (IV) Oxide was added slowly to 5.0 liters $H_2O$ and heated to 140° F. Solution was stirred about 30 minutes.

A carbohydrate media containing 5.0 kilograms Maltose and 10.0 kilograms Gum Acacia were added to a 50 liters $H_2O$ and heated to 140° F. Solution was stirred about 30 minutes.

A nutrient solution was than added to a carbohydrate medial solution, and stirred at 130–140° F. for 3 hours. This solution than allowed to cool to 95+/−2° F.

An active yeast solution was than prepared. 22.7 kilograms of active baker's yeast, *Saccharomyces cervisiae* (~10 billion colony forming units per gram) was added to 120 liters $H_2O$ and stirred for 30 minutes.

The nutrient (Selenium) and carbohydrate media then inoculated very slowly into the active yeast solution to form a live fermented solution. The mixture was allowed to ferment for two hours at 90–95° F. 48.144 kilograms nutritional yeast (inactive yeast) was added and mixture was allowed to ferment for one hour at 90–95° F. 12.344 kilogram soy flour (non-GMO) was added and mixture was allowed to ferment for one hour at 90–95° F. 500 grams proteolytic enzyme (Papain) was then added and allowed to react for 30 minutes.

1000 grams *Lactobacillus acidophillus* and *Bacterium bifidus* (~4 billion colony forming units per gram) were added to the live fermented solution and allowed to ferment for 1 and ½ hours at 90–95° F. with constant stirring. Active fermentation was then stopped by heating the solution to 160–170° F. for three hours with stirring.

The solution was then homogenized in a shearing pump and spray dried. The resulting product was fine brown to tan powder, which was analyzed for potency and bioactivity.

EXAMPLE 5

The bioactivity of a composition of the invention produced in Example 4 containing selenium as an active ingredient was then examined relative to commercially available selenium. The methods used were as set forth in Example 2.

Selenomethionine and sodium selenite samples were obtained from Sigma and a sample of the invention containing selenium (2000 $\mu$g/g). The samples were dissolved in water and added at concentrations from 0.1 to 100 $\mu$M to the LDL+VLDL preparations (in vitro model of heart disease) as described in Example 2.

The LDL and VLDL preparations were then oxidized for 6 hours with cupric ion and the oxidation products measured by fluorometry of thiobarbituric acid-reactive substances. The concentration of selenium to inhibit the oxidation 50% was calculated (IC50) and I/IC50 calculated in order to compare results. The greater the value of I/IC50, the better the quality of antioxidants. The results are set forth in Table 3.

TABLE 3

| Sample | IC50 | I/IC50 |
| --- | --- | --- |
| Sodium selenite | >100 µM | <1 |
| Selenomethionine | 27 µM | 3.7 |
| Selenium Yeast | 0.42 µM | 238 |

The results demonstrated that the selenium associated with the composition of the invention was a vastly superior antioxidant. Sodium selenite exhibited no antioxidant activity and the composition of the invention was 64 times better as an antioxidant than selenomethionine.

What is claimed is:

1. A composition comprising a mineral bound by a glycoprotein matrix, wherein said composition is obtained by a process comprising:
   i) adding a mineral to a water based nutrient media containing carbohydrates and *Saccharomyces cerevisiae*, and fermenting to obtain a first fermented solution,
   ii) adding a proteolytic enzyme to the first fermented solution obtained from part (i),
   iii) adding *Lactobacillus acidophilus* and *Bacterium bifidus* to the first fermented solution containing the proteolytic enzyme of part (ii) and fermenting to obtain the final fermented solution; and
   iv) drying the final fermented solution obtained from part (iii).

2. The composition according to claim 1, wherein the nutrient media further comprises a bioflavanoid.

3. The composition according to claim 1, wherein the solution is dehydrated by spray drying.

4. The composition according to claim 1, wherein the process further comprises homogenizing the solution prior to drying.

5. The composition according to claim 1, wherein the *L. acidophilus* and *S. cerevisiae* are deactivated prior to drying.

6. The composition according to claim 1, wherein the mineral is selenium.

7. The composition according to claim 1, wherein the mineral is chromium.

8. The composition according to claim 1, wherein the mineral is zinc.

9. The composition according to claim 1, wherein the mineral is iron.

10. A nutritional supplement comprising the composition according to claim 1.

* * * * *

UNITED STATES PATENT AND TRADEMARK OFFICE
CERTIFICATE OF CORRECTION

PATENT NO. : 6,864,231 B2
DATED : March 8, 2005
INVENTOR(S) : Dilip Chokshi

It is certified that error appears in the above-identified patent and that said Letters Patent is hereby corrected as shown below:

<u>Column 1,</u>
Line 44, now reads "cooper absorption,"
      should read -- copper absorption --.

<u>Column 3,</u>
Lines 29-30, now reads "The protein of the glycoprotein can any suitable polypeptide"
      should read -- The protein of the glycoprotein can be any suitable
      polypeptide --.

<u>Column 7,</u>
Line 9, now reads "four, non-genetically"
      should read -- flour, non-genetically --.

Signed and Sealed this

Ninth Day of August, 2005

JON W. DUDAS
*Director of the United States Patent and Trademark Office*